(12) United States Patent
Wang et al.

(10) Patent No.: US 8,907,147 B2
(45) Date of Patent: Dec. 9, 2014

(54) SYNTHESIS OF 1,1,2,3-TETRACHLOROPROPENE

(71) Applicant: Honeywell International Inc., Morristown, NJ (US)

(72) Inventors: Haiyou Wang, Amherst, NY (US); Hsueh Sung Tung, Getzville, NY (US); Joshua Close, Blasdell, NY (US); Terris Tianxue Yang, East Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/168,044

(22) Filed: Jan. 30, 2014

(65) Prior Publication Data
US 2014/0221705 A1    Aug. 7, 2014

Related U.S. Application Data

(60) Provisional application No. 61/760,450, filed on Feb. 4, 2013.

(51) Int. Cl.
| | |
|---|---|
| *C07C 17/25* | (2006.01) |
| *C07C 17/358* | (2006.01) |
| *C07C 17/02* | (2006.01) |
| *C07C 17/10* | (2006.01) |

(52) U.S. Cl.
CPC ............... *C07C 17/358* (2013.01); *C07C 17/02* (2013.01); *C07C 17/10* (2013.01); *C07C 17/25* (2013.01)
USPC ............ 570/220; 570/227; 570/228; 570/229

(58) Field of Classification Search
CPC .......... C07C 17/25; C07C 17/10; C07C 17/02
USPC ................................ 570/220, 227, 228, 229
See application file for complete search history.

(56) References Cited

U.S. PATENT DOCUMENTS

| | | |
|---|---|---|
| 3,926,758 A | 12/1975 | Smith |
| 4,650,914 A | 3/1987 | Woodard |
| 7,094,936 B1 | 8/2006 | Owens et al. |
| 8,115,038 B2 | 2/2012 | Wilson et al. |
| 8,258,355 B2 | 9/2012 | Merkel et al. |
| 2004/0225166 A1 | 11/2004 | Wilson et al. |
| 2009/0216055 A1 | 8/2009 | Wilson et al. |
| 2011/0118513 A1 | 5/2011 | Smith et al. |
| 2012/0035402 A1 | 2/2012 | Wilson et al. |
| 2012/0289751 A1 | 11/2012 | Nose et al. |

FOREIGN PATENT DOCUMENTS

JP        53144509 A1    12/1978

OTHER PUBLICATIONS

Espacenet—Bibliographic data for JP 53144509A—English Language Abstract.
PCT ISR & Written Opinion issued in PCT/US2014/014366 dated Apr. 7, 2014.

*Primary Examiner* — Elvis O Price
(74) *Attorney, Agent, or Firm* — Bruce O. Bradford

(57) ABSTRACT

The present invention provides an improved process for producing 1,1,2,3-tetrachloropropene. By using a first reactive distillation column for HCC-250fb dehydrochlorination, and a second reactive distillation column for HCC-240db dehydrochlorination/HCC-1230xf isomerization, the 1,1,2,3-tetrachloropropene manufacturing process can be greatly simplified, resulting in reduced equipment use, energy use, as well as increased productivity.

15 Claims, 1 Drawing Sheet

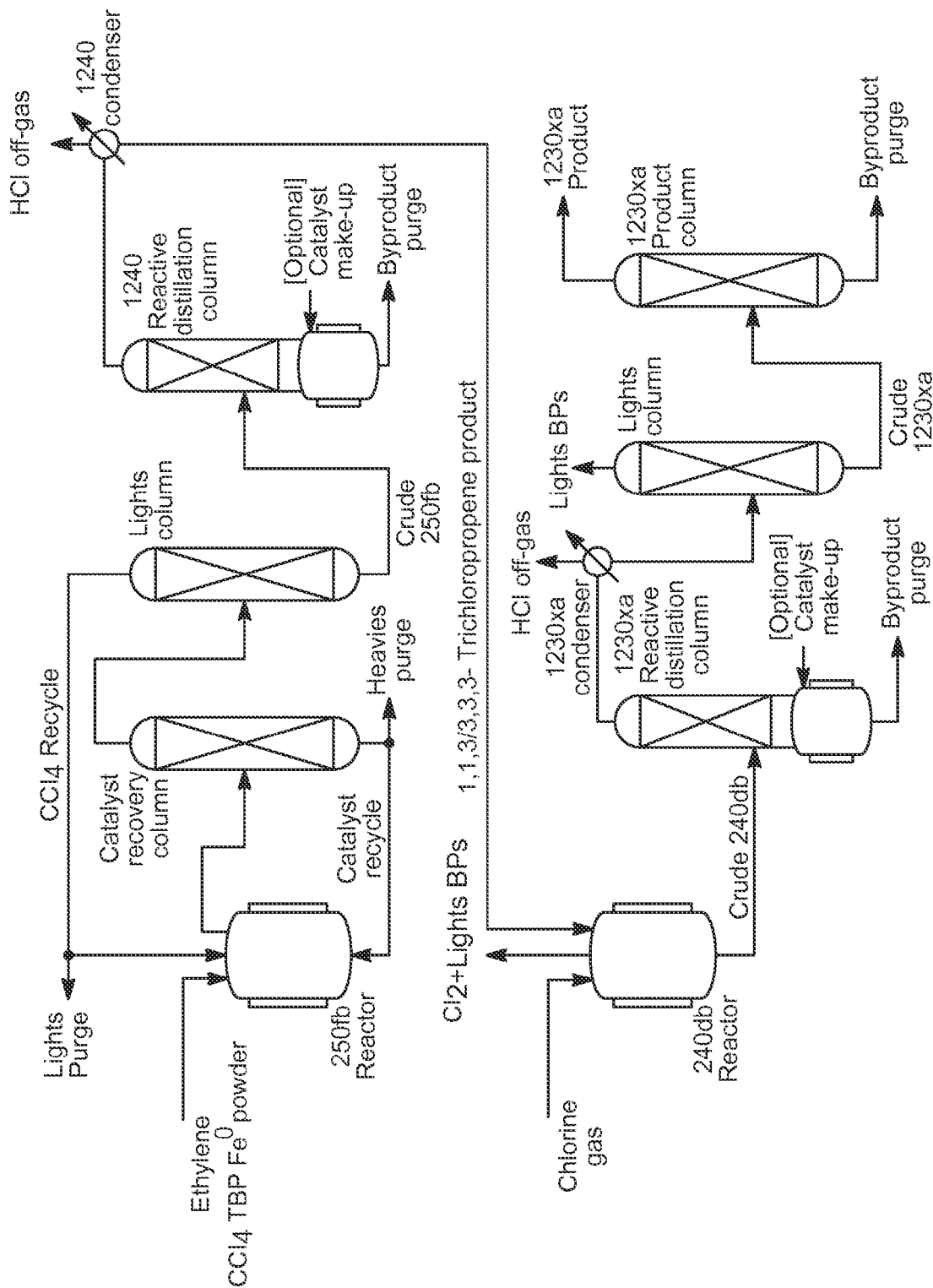

SYNTHESIS OF 1,1,2,3-TETRACHLOROPROPENE

CROSS-REFERENCE TO RELATED APPLICATION

This application claims benefit of U.S. Provisional Patent Application Ser. No. 61/760,450 filed Feb. 4, 2013, the disclosure of which is hereby incorporated herein by reference.

FIELD OF THE INVENTION

This invention relates to the production of a haloolefin, more specifically a chloroolefin, and particularly, 1,1,2,3-tetrachloropropene.

BACKGROUND OF THE INVENTION

As disclosed in U.S. Pat. No. 8,058,486, the compound 1,1,2,3-tetrachloropropene (HCC-1230xa) is an important precursor that can be used for the production of 2,3,3,3-tetrafluoropropene (HFO-1234yf), which is a low GWP molecule that can be used as an effective refrigerant, fire extinguishing agent, heat transfer medium, propellant, foaming agent, blowing agent, gaseous dielectric agent, sterilant carrier, polymerization medium, particulate removal fluid, carrier fluid, buffing abrasive agent, displacement drying agent and power cycle working fluid, to name but a few.

Methods for making 1,1,2,3-tetrachloropropene (HCC-1230xa) are known. For example, U.S. Pat. No. 4,650,914 provides a multi-step process in which 1,1,1,3-tetrachloropropane is generated, purified, and fed to a dehydrochlorination reactor to produce two trichloropropene isomers, namely 1,1,3- and 3,3,3-trichloropropenes ((HCC-1240za and HCC-1240zf, respectively). As shown below, in steps (4) and (5) of the process, the compound 1,1,2,3-tetrachloropropene (HCC-1230xa) is formed.
The steps are:

(1) preparing 1,1,1,3-tetrachloropropane by reacting ethylene with carbon tetrachloride in the presence of both a source of metallic iron that is effective as an activator for the reaction, and a promoter for the reaction, said promoter being selected from organic phosphite and organic phosphate compounds;

(2) dehydrochlorinating the 1,1,1,3-tetrachloropropane to produce a mixture of 1,1,3- and 3,3,3-trichloropropenes;

(3) chlorinating at least one of the trichloropropenes obtained by the dehydrochlorination step to produce 1,1,1,2,3-pentachloropropane;

(4) dehydrochlorinating the 1,1,1,2,3-pentachloropropane to produce a mixture of 1,1,2,3- and 2,3,3,3-tetrachloropropenes; and (5) contacting the mixture of tetrachloropropenes with anhydrous ferric chloride acting as an allylic rearrangement catalyst, thereby converting the 2,3,3,3-tetrachloropropene to 1,1,2,3-tetrachloropropene.

In Step 1 of the '914 process, carbon tetrachloride is reacted with ethylene in the presence of iron and a phosphorus (V) compound containing a phosphoryl group, preferably an alkyl phosphate chelating agent (such as tributyl phosphate) to form 1,1,1,3-tetrachloropropane. Next, the 1,1,1,3-tetrachloropropane product is fed to a Step 2 dehydrochlorination reactor that contains a base. The resulting products are subject to phase separation and the organic phase containing 1,1,3-trichloropropene (HCC-1240za) and 3,3,3-trichloropropene (HCC-1240zf) was used directly in the next step.

In Step 3 of the '914 process, the trichloropropene mixture is reacted with chlorine to form 1,1,1,2,3-pentachloropropane (HCC-240db). Next, the HCC-240db product is fed to a Step 4 dehydrochlorination reactor that contains a base to form a mixture of 1,1,2,3- and 2,3,3,3-tetrachloropropenes.

In Step (5) the compound 2,3,3,3-tetrachloropropene (HCC-1230xf) is isomerized to 1,1,2,3-tetrachloropropene (HCC-1230xa) in the presence of a Lewis acid catalyst, particularly ferric chloride.

The present invention provides improvements to this reaction scheme, whereby the desired product 1,1,2,3-tetrachloropropene (HCC-1230xa) is formed with less capital expense.

SUMMARY OF THE INVENTION

The present invention is based on the discovery that the multi-step process described in the '914 patent can be consolidated if a "reactive distillation column" is utilized together with a judiciously selected solid catalyst.

In one embodiment, the present invention provides an improved process for producing 1,1,2,3-tetrachloropropene (HCC-1230xa). By using a first reactive distillation column charged with a Lewis acid catalyst for HCC-250fb dehydrochlorination, and a second reactive distillation column charged with a Lewis acid catalyst for HCC-240db dehydrochlorination/HCC-1230xf isomerization, the 1,1,2,3-tetrachloropropene manufacturing process can be greatly simplified, resulting in reduced equipment use, energy use, as well as increased productivity.

BRIEF DESCRIPTION OF THE DRAWING

FIG. 1 shows one process configuration for the manufacture of 1,1,2,3-tetrachloropropene.

DETAILED DESCRIPTION OF THE INVENTION

As disclosed in U.S. Pat. No. 4,650,914, the compound 1,1,2,3-tetrachloropropene (HCC-1230xa) can be produced from carbon tetrachloride ($CCl_4$) and ethylene ($CH_2CH_2$) via the following five steps:

(1) $CCl_4 + CH_2=CH_2 \rightarrow CCl_3CH_2CH_2Cl$ (HCC-250fb) in a liquid phase in the presence of a catalyst system comprising iron, ferric chloride and a chelating agent such as triethyl phosphate or tributyl phosphate, (2) $CCl_3CH_2CH_2Cl \rightarrow CCl_2=CHCH_2Cl$ (HCC-1240za) + $CCl_3CH=CH_2$ (HCC-1240zf) + 2 HCl in a liquid phase reactor in the presence of caustic solution, (3) $CCl_2=CHCH_2Cl + CCl_3CH=CH_2 + 2\ Cl_2 \rightarrow 2\ CCl_3CHClCH_2Cl$ (HCC-240db) in a photo-chlorination reactor, (4) $CCl_3CHClCH_2Cl \rightarrow CCl_2=CClCH_2Cl$ (HCC-1230xa) + $CCl_3CCl=CH_2$ (HCC-1230xf) + HCl in a liquid phase reactor in the presence of caustic solution, and (5) $CCl_3CCl=CH_2$ (HCC-1230xf) $\rightarrow CCl_2=CClCH_2Cl$ (HCC-1230xa) in a liquid phase reactor in the presence of an isomerization catalyst such as ferric chloride.

The present invention can be generally described as an improved manufacturing process for producing HCC-1230xa, in which a first reactive distillation column charged with a Lewis acid catalyst is used for HCC-250fb dehydrochlorination, and a second reactive distillation column charged with a Lewis acid catalyst for HCC-240db dehydrochlorination/HCC-1230xf isomerization. The improved manufacturing process is schematically illustrated in FIG. 1.

In Step 1, the reaction of carbon tetrachloride and ethylene is carried out in a glass-lined reactor, which is equipped with an agitator. In one embodiment, $CCl_4$ liquid and ethylene vapor are continuously fed into reactor at desired ratio through a diffusing device such as a dip tube, or more preferably, through a sponge type gas diffuser. By doing so, the contact surface between ethylene vapor and $CCl_4$ liquid is increased, which improves the reactivity. The reaction of ethylene and carbon tetrachloride to form HCC-250fb is preferably initiated utilizing iron powder as the catalyst and an organo-phosphate compound such as tributylphosphate (TBP) as the co-catalyst. While batch processing can be used for the reactions, it is preferred that continuous manufacturing processing is used herein.

The iron powder is preferably a fine powder of pure metallic iron, preferably with a particle size smaller than 325 mesh, but other mesh sizes can be used if so desired. Iron powder and TBP can be added into reactor periodically or continuously, but the continuous mode is preferred. Iron powder may be added to the reactor by any means, but powder slurry in carbon tetrachloride, in TBP, or in the mixture of both is preferred. While iron powder is preferred, any iron object can be used, such as iron balls, iron wire, iron shavings, and the like.

The co-catalyst TBP is a chelating agent and also serves as solvent to help dissolve the solid catalyst. The mole ratio of iron powder to TBP may be about 0.05:1 to about 500.0:1, preferably about 1.0:1 to about 100.0:1, and more preferably about 1.5:1 to about 10:1. The preferred concentration of the catalyst in the reaction mixture is from about 0.001 to about 20 weight percent, preferably from about 0.01 to about 10 weight percent, and more preferably from about 0.1 to about 5 weight percent. Additional organophosphate compounds useful herein as co-catalysts include the following: triphenylphosphate, tributylphosphate, triethylphosphate, trimethylphosphate, tripropylphosphate or any other similar organophosphate compound, and mixtures of two or more of these compounds.

Generally, the mole ratio of $CCl_4$ to ethylene is from about 0.02:1 to about 50:1. Preferably, the ratio is from about 0.1:1 to about 4.0:1 and more preferably from about 1:1 to about 3:1. The reaction can be operated at a temperature ranged from about 40° C. to about 180° C., preferably from about 85° C. to about 150° C., with agitation. The reaction temperature and catalytic activity inherently determine the reactor pressure, which is preferably from 50 psia to 120 psia. The reaction is preferably carried out at a residence time of from about 0.01 hours to about 24 hours, preferably from about 1 hour to about 12 hours. The reaction conditions are selected for high ethylene efficiency, high HCC-250fb yield, and low by-products production.

In continuous operation, reactor contents are continually drawn through a tube immersed into liquid. After going through a filter where iron particles are trapped, reactor effluent stream is fed to a Catalyst Recovery Column (CRC) to separate into a "top" stream comprising unreacted $CCl_4$ and ethylene (if any) feed materials and the HCC-250fb reaction product with low concentration of heavy byproducts, and a "bottom" stream comprising catalyst/co-catalyst and some heavy byproducts such as 1,1,1,5-tetrachloropentane and its isomers. The CRC column is preferably conducted at a temperature less than the reaction temperature and under vacuum.

The "top" stream from CRC column is then fed to a lights distillation column for further separation, optionally at atmospheric but preferably under vacuum (about 5 to about 200 mm Hg). The distilled $CCl_4$ and ethylene may be recycled back to the reactor. The distilled HCC-250fb, which is substantially free of $CCl_4$ and lights byproducts, can be directly used as raw material for Step 2. The "bottom" stream from CRC column is recycled back to the reactor. Periodical purges may be applied to avoid accumulation of heavy by-products such as 1,1,1,5-tetrachloropentane and its isomers in the catalyst recycle stream.

In Step 2 of the present inventive process, a first reactive distillation column, which comprises a reaction zone, a separation zone, and a condensation zone, is used for HCC-250fb dehydrochlorination. The HCC-250fb feed is introduced to the first reactive distillation column charged with a Lewis acid catalyst, in which the generated $CCl_2$=$CHCH_2Cl$ and/or $CCl_3CH$=$CH_2$ as well as HCl are removed from the reaction zone by distillation during the course of the dehydrochlorination of HCC-250fb. The reactive distillation column is preferably operated in such a way that both feed addition and product removal are continuous and simultaneous. In order to avoid the accumulation of some heavy byproducts such as pentachlorocyclohexenes and hexachloro-cyclohexanes, continuous or periodical purge of reaction content is performed. The material purged out can be sent to a batch distillation to recover useful compounds such as 250fb, $CCl_2$=$CHCH_2Cl$ and/or $CCl_3CH$=$CH_2$.

The Lewis acid catalyst may serve as dehydrochlorination catalyst for HCC-250fb dehydrochlorination. Non-limiting examples of Lewis acid catalysts include, but are not limited to, metal halides such as $FeCl_3$, $FeF_3$, $AlCl_3$, $AlF_3$, and the like, and halogenated metal oxides such as chlorinated $Fe_2O_3$, fluorinated $Fe_2O_3$, chlorinated $Al_2O_3$, fluorinated $Al_2O_3$ and the like. Agitation in reaction zone is preferred to help the mixing of catalyst and reagent, which can be achieved by stirring or through pumped circulation loops. Any conventional means can be used to introduce catalyst. In one embodiment, the said Lewis acid catalyst is continuously fed to the reaction zone of the first reactive distillation column together with HCC-250fb feed. Yet, in another embodiment, the said Lewis acid catalyst is periodically and separately added to the reaction zone of the first reactive distillation column.

The dehydrochlorination of 1,1,1,3-tetrachloropropane (HCC-250fb) can be carried out under ambient pressure or vacuum condition (50-760 mm Hg preferably 100-380 mm Hg) and at a temperature of 80° C. to 130° C. (preferably 100° C. to 120° C.), with a catalyst/250fb ratio of 50 to 5000 ppmw (preferably 100 to 1500 ppmw) and a residence time of 0.5 to 8 hours (preferably 2 to 6 hours).

The distilled product stream comprising generated $CCl_2$=$CHCH_2Cl$ and/or $CCl_3CH$=$CH_2$ as well as HCl from the first reactive distillation column is fed to a condenser for HCl and organic separation. In certain embodiments, the condensation takes place using a low-temperature refrigerant brine at temperatures ranging from −80° C. to ambient. The pressure is appropriate to allow for organic condensation at the chosen temperature while allowing the HCl to remain as a vapor. The condensed organic comprising $CCl_2$=$CHCH_2Cl$ and/or $CCl_3CH$=$CH_2$ is fed to Step 3 reactor for reaction. The HCl vapor can be further recovered using a compressor or removed using a caustic solution scrubber.

In Step 3, the chlorination of 1,1,3-trichloropropene/3,3,3-trichloropropene is carried out in a reactor equipped with an agitator, a $Cl_2$ gas distributor/sparger and a total condenser. At the startup, the reactor is charged with certain amount of 1,1,3-trichloropropene/3,3,3-trichloropropene, and heated up to the designated reaction temperature (room temperature to 120° C., preferably 60° C. to 90° C.). $Cl_2$ gas is then fed into the reactor to have 1,1,3-trichloropropene/3,3,3-trichloropropene chlorinated to 240db, The $Cl_2$ feed rate is controlled in such a way that the reactor temperature is maintained at ±5° C. of the set reaction temperature. After all 1,1,3-trichloropropene/3,3,3-trichloropropene has been converted to 240db (normally in 1 to 6 hours, preferably 2 to 4 hours), a continuous feed of 1,1,3-trichloropropene/3,3,3-trichloropropene is introduced into the reactor, with corresponding $Cl_2$ gas feed rate adjusted to 100 to 150 mol % (preferably 110-120 mol %) of 1,1,3-trichloropropene/3,3,3-trichloropropene feed rate, and crude HCC-240db is continuously drawn-off from the reactor as the raw material for next step reaction.

In Step 4 of the present inventive process, a second reactive distillation column, which comprises a reaction zone, a separation zone, and a condensation zone, is used for HCC-240db dehydrochlorination/HCC-1230xf isomerization. The HCC-240db feed is introduced to the second reactive distillation column charged with a Lewis acid catalyst, in which the generated HCC-1230xa and HCl are removed from the reaction zone by distillation during the course of the dehydrochlorination of HCC-240db to HCC-1230xa and HCC-1230xf/ the isomerization of HCC-1230xf to HCC-1230xa. The reactive distillation column is preferably operated in such a way that both feed addition and product removal are continuous and simultaneous. In order to avoid the accumulation of some heavy byproducts such as pentachlorocyclohexenes and hexachlorocyclohexanes, continuous or periodical purge of reaction content is performed. The material purged out can be sent to a batch distillation to recover useful compounds such as HCC-240db, and HCC-1230xa.

The Lewis acid catalyst may serve as dehydrochlorination catalyst for HCC-240db dehydrochlorination and isomerization catalyst for HCC-1230xf isomerization simultaneously. Non-limiting examples of Lewis acid catalysts include, but are not limited to, metal halides such as $FeCl_3$, $FeF_3$, $AlCl_3$, $AlF_3$, and the like, and halogenated metal oxides such as chlorinated $Fe_2O_3$, fluorinated $Fe_2O_3$, chlorinated $Al_2O_3$, fluorinated $Al_2O_3$ and the like. Agitation in reaction zone is preferred to help the mixing of catalyst and reagent, which can be achieved by stirring or through pumped circulation loops. Any conventional means can be used to introduce catalyst. In one embodiment, the said Lewis acid catalyst is continuously fed to the reaction zone of the second reactive distillation column together with HCC-240db feed. Yet, in another embodiment, the said Lewis acid catalyst is periodically and separately added to the reaction zone of the second reactive distillation column.

The dehydrochlorination of HCC-240db or the isomerization of HCC-1230xf can be carried out under ambient pressure or vacuum condition (50-760 mm Hg, preferably 100-380 mm Hg) and at a temperature of 80° C. to 130° C. (preferably 100° C. to 120° C.), with a catalyst/240db ratio of 1000 to 50000 ppmw (preferably 5000 to 20000 ppmw) and a residence time of 0.5 to 8 hours (preferably 1 to 3 hours).

The distilled product stream comprising generated HCC-1230xa and HCl from the second reactive distillation column is fed to a condenser for HCl and organic separation. In certain embodiments, the condensation takes place using a low-temperature refrigerant brine at temperatures ranging from −80° C. to ambient. The pressure is appropriate to allow for condensation at the chosen temperature while allowing the HCl to remain as a vapor. The condensed organic comprising HCC-1230xa is fed to one or more distillation columns for further purification so as to meet specifications required for the use as raw material for making HFO-1234yf. The HCl vapor can be further recovered using a compressor or removed using a caustic solution scrubber.

The following are examples of the invention, which are not to be construed as limiting.

EXAMPLE 1

HCC-250fb Synthesis

Approximately 35 lbs of carbon tetrachloride was mixed with 0.35 lbs of tributyl phosphate and 167 g of 325 mesh iron powder into a nitrogen purged 5 gallon glass-lined reactor. The reactor temperature was raised to 80° C. and vented of non-condensables. At temperature, a continuous ethylene feed of about 0.5-0.7 lbs/hr was introduced into the liquid carbon tetrachloride mixture. The temperature of the reactor was raised to 100° C. as a result of the reaction exotherm. Cooling water was used to maintain the reaction temperature at 100° C. After about 6.8 hrs, the reaction was terminated and yielded a net ethylene consumption of 3.8 lbs. The 1,1,1,3-tetrachloropropane (250fb) selectivity was observed to be 95% with a carbon tetrachloride single-pass conversion of 70%.

EXAMPLE 2

Catalyst Recovery Column Operation

Reaction material from Example 1 was fed continuously at a rate of about 2 lbs/hr to a Monel, 3 inch diameter vacuum flash column (Catalyst Recovery Column) equipped with a double-pipe reboiler and a shell and tube condenser. The column was operated at about 1-2 psia with a reboiler temperature of about 95° C. to 105° C. At this condition, distillate material was collected and observed to be composed of, on average, 70.0 wt % 250fb, 29.0 wt % carbon tetrachloride, and a balance of both lights and heavies byproducts.

EXAMPLE 3

Lights Separation Crude HCC-250fb Product

About 1.5 L of crude 250fb distillate material from Example 2 was loaded into lab scale distillation apparatus. The apparatus was equipped with a 3 L round-bottom flask reboiler, a 20-stage sieve tray column with an evacuated jacket, a condenser with cooling water, an external reflux splitter, and a 300 mL distillate collection flask. The reboiler was heated using a mantle and Variac until the appropriate boil-up was achieved. Lights removal was carried out with a reflux ratio of 1. During distillation, the temperature at reboiler slowly climbed from 109° C. to 200° C. as the concentration of lights in the crude product was reduced. Similarly, the column top temperature also increased from 74° C. to 160° C. The distillation was terminated once the top temperature reached about 160° C. The reboiler contents was collected and observed to be composed of 98.6 wt % 250fb with the balance of heavies byproducts.

EXAMPLE 4

HCC-1240 Synthesis and Separation

A 1000 ml reactor equipped with an agitator, a distillation column and a condenser is charged with a mixture of HCC-250fb (500 g, 99.1 wt % pure) and $FeCl_3$ (0.125 g, Anhydrous). A vacuum pump is connected to the condenser through a KOH scrubber and an acid trap to adjust the system pressure during the operation. At the startup, the system pressure is maintained at 250 mm HgVac and the condenser is set to total reflux mode. The reactor is heated to a temperature of 120° C. using an oil bath, and the oil bath temperature is adjusted to maintain the reactor temperature at 120° C.±2° C. After 4 hours, a continuous feed of the mixture of 250fb and FeCl3 (250 ppmw of $FeCl_3$/250fb) is introduced into the reactor. At the same time, 1,1,3-trichloropropene is taken off as the product from the exit of the condenser while maintaining a certain reflux ratio, and HCl generated in the reaction remains in the off-gas and is absorbed by KOH solution in the scrubber. A mixture of 1,1,3-trichloropropene, 250fb and other impurities is drawn off from the bottom of the reactor to maintain an appropriate ratio of $FeCl_3$/250fb in the reactor. The flow rates for both streams are adjusted to maintain a residence time of 4 hours.

Depending on the operating conditions, the product stream normally contains 99.5-100 wt % of 1,1,3-trichloropropene which can be used as the raw material for the next step reaction, and the bottom draw-off stream contains 10-40 wt % of 1,1,3-trichloropropene, 50-80 wt % of 250fb, 0-10 wt % of heavies (due to the dimerization of 250fb and/or 1,1,3-trichloropropene) and the catalyst $FeCl_3$. The bottom draw-off stream can be either recycled back to the feed tank or stored to further recover the useful compounds (such as 1,1,3-trichloropropene and 250fb). The single pass conversion for the 250fb is about 60-70 mol %, and the selectivity to 1,1,3-trichloropropene is >95 mol %.

EXAMPLE 5

HCC-240db Synthesis

A 500 ml reactor equipped with an $Cl_2$ gas sparger and a total condenser was charged with 250 g of 1,1,3-trichloropropene (99.5 wt % pure). The reactor was stirred and heated using an oil bath which had been preheated to 80° C. After the reactor temperature reached 80° C., $Cl_2$ gas was fed into the reactor via the gas sparger. The reactor temperature was controlled at 80° C.±5° C. by controlling the feed rate of $Cl_2$ gas and adjusting the oil bath temperature setting. During the operation, the total $Cl_2$ feed was maintained at 110-120 mol % of 1,1,3-trichloropropene charged into the reactor. After 2 hours, $Cl_2$ feed was stopped and the reactor was cooled down to room temperature. The conversion of 1,1,3-trichloropropene was 99.6 mol %, with the selectivity to 240db being 97.3 mol %.

EXAMPLE 6

HCC-1230xa Synthesis and Separation

A 1000 ml reactor equipped with an agitator, a distillation column and a condenser is charged with a mixture of HCC-240db (500 g, 95.1 wt % pure, a product from previous step reaction) and $FeCl_3$ (5.0 g, Anhydrous) is charged to the same apparatus as described in Example 1. At the startup, the system pressure is maintained at 150 mm Hg and the condenser is set to total reflux mode. The reactor is heated to a temperature of 120° C. using an oil bath, and the oil bath temperature is adjusted to maintain the reactor temperature at 120° C.±2° C. After 2 hours, a continuous feed of the mixture of 240db and $FeCl_3$ (10000 ppmw of $FeCl_3$/240db) is introduced into the reactor. At the same time, 1,1,2,3-tetrachloropropene is taken off as the product from the exit of the condenser while maintaining a certain reflux ratio, and HCl generated in the reaction remains in the off-gas and is absorbed by KOH solution in the scrubber. A mixture of 1,1,2,3-tetrachloropropene, 240db and other impurities is drawn off from the bottom of the reactor to maintain an appropriate ratio of $FeCl_3$/240db in the reactor. The flow rates for both streams are adjusted to maintain a residence time of 2 hours.

Depending on the operating conditions, the organic portion of the product stream normally contains >99.9 wt % of 1,1,2,3-tetrachloropropene, and the bottom draw-off stream contains 80-85 wt % of 1,1,2,3-tetrachloropropene, 5-10 wt % of 240db, 5-10 wt % of other organic impurities and the catalyst $FeCl_3$. The bottom draw-off stream can be either recycled back to the feed tank or stored for the further recovery of the useful compounds (such as 1,1,2,3-tetrachloropropene and 240db). The single pass conversion for the 240db is >95 mol %, and the selectivity to 1,1,2,3-tetrachloropropene is >97 mol %.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. In a method for producing 1,1,2,3-tetrachloropropene (HCC-1230xa), which includes the following steps:
   (1) preparing 1,1,1,3-tetrachloropropane by reacting ethylene with carbon tetrachloride in the presence of both a source of metallic iron that is effective as an activator for the reaction, and a promoter for the reaction, said promoter being selected from phosphorus (V) compounds containing a phosphoryl group;
   (2) dehydrochlorinating the 1,1,1,3-tetrachloropropane to produce a mixture of 1,1,3- and 3,3,3-trichloropropenes;
   (3) chlorinating at least one of the trichloropropenes obtained by the dehydrochlorination step to produce 1,1,1,2,3-pentachloropropane;
   (4) dehydrochlorinating the 1,1,1,2,3-pentachloropropane to produce a mixture of 1,1,2,3- and 2,3,3,3-tetrachloropropenes; and
   (5) contacting the mixture of tetrachloropropenes with anhydrous ferric chloride acting as an allylic rearrangement catalyst, thereby converting the 2,3,3,3-tetrachloropropene to 1,1,2,3-tetrachloropropene;
   the improvement comprising;
   using a first reactive distillation column for HCC-250fb dehydrochlorination, and a second reactive distillation column for HCC-240db dehydrochlorination/HCC-1230xf isomerization.

2. The process of claim 1, wherein Step (1) is conducted in the liquid phase in the presence of a catalyst system comprising iron, ferric chloride and a promoter comprising one or more chelating agents.

3. The process of claim 2, wherein Step (1) is modified such that the crude reaction material is fed directly to a reactive distillation unit containing an effective amount of a dehydrochlorination catalyst.

4. The process of claim 2, wherein the dehydrochlorination catalyst can either exist within column internals (packing or trays) and/or be added to the reboiler or column sump.

5. The process of claim 3, wherein the dehydrochlorination catalyst comprises one or more metal halides.

6. In a method for producing 1,1,2,3-tetrachloropropene (HCC-1230xa), which includes the following steps:
   (1) preparing 1,1,1,3-tetrachloropropane by reacting ethylene with carbon tetrachloride in the presence of both a source of metallic iron that is effective as an activator for the reaction, and a promoter for the reaction, said promoter being selected from trialkyl phosphates or trialkyl phosphites;
   (2) dehydrochlorinating the 1,1,1,3-tetrachloropropane to produce a mixture of 1,1,3- and 3,3,3-trichloropropenes;
   (3) chlorinating at least one of the trichloropropenes obtained by the dehydrochlorination step to produce 1,1,1,2,3-pentachloropropane;
   (4) dehydrochlorinating the 1,1,1,2,3-pentachloropropane to produce a mixture of 1,1,2,3- and 2,3,3,3-tetrachloropropenes; and
   (5) contacting the mixture of tetrachloropropenes with anhydrous ferric chloride acting as an allylic rearrangement catalyst, thereby converting the 2,3,3,3-tetrachloropropene to 1,1,2,3-tetrachloropropene;
   the improvement comprising;
      using a first reactive distillation column for HCC-250fb dehydrochlorination, and a second reactive distillation column for HCC-240db dehydrochlorination/HCC-1230xf isomerization.

7. The process of claim 6, wherein Step (4) takes place in a liquid phase reactor in the presence of caustic solution or a dehydrochlorination catalyst.

8. The process of claim 6, wherein Step (5) takes place in a liquid phase reactor in the presence of an isomerization catalyst.

9. In a method for producing 1,1,2,3-tetrachloropropene (HCC-1230xa), which includes the following steps:
   (1) preparing 1,1,1,3-tetrachloropropane by reacting ethylene with carbon tetrachloride in the presence of both a source of metallic iron that is effective as an activator for the reaction, and a promoter for the reaction, said promoter being selected from trialkyl phosphates;
   (2) dehydrochlorinating the 1,1,1,3-tetrachloropropane to produce a mixture of 1,1,3- and 3,3,3-trichloropropenes;
   (3) chlorinating at least one of the trichloropropenes obtained by the dehydrochlorination step to produce 1,1,1,2,3-pentachloropropane;
   (4) dehydrochlorinating the 1,1,1,2,3-pentachloropropane to produce a mixture of 1,1,2,3- and 2,3,3,3-tetrachloropropenes; and
   (5) contacting the mixture of tetrachloropropenes with anhydrous ferric chloride acting as an allylic rearrangement catalyst, thereby converting the 2,3,3,3-tetrachloropropene to 1,1,2,3-tetrachloropropene;
   the improvement comprising;
      combining the process of Step (1) with the process of Step (2) such that the crude product formed in Step (1) the dehydrochlorination process of Step (2) are combined in a single reactive column; and
      combining the dehydrochlorination reaction of Step (4) with the process of Step (5) in a single reactive column.

10. The process of claim 9, wherein Step (1) is conducted in the liquid phase in the presence of a catalyst system comprising iron, ferric chloride and a chelating agent.

11. The process of claim 10, wherein Step (1) is modified such that the crude reaction material is fed directly to a reactive distillation unit containing an effective amount of a dehydrochlorination catalyst.

12. The process of claim 10, wherein the dehydrochlorination catalyst can either exist within column internals (packing or trays) and/or be added to the reboiler or column sump.

13. The process of claim 11, wherein the dehydrochlorination catalyst comprises one or more metal halides.

14. The process of claim 9, wherein Step (4) takes place in a liquid phase reactor in the presence of caustic solution or a dehydrochlorination catalyst.

15. The process of claim 9, wherein Step (5) takes place in a liquid phase reactor in the presence of an isomerization catalyst.

* * * * *